US008663271B2

(12) United States Patent
Mantell (10) Patent No.: US 8,663,271 B2
(45) Date of Patent: Mar. 4, 2014

(54) IN-DWELLING PORT FOR ACCESS INTO A BODY (75) Inventor: Robert R. Mantell, Arlington, IL (US)

(73) Assignee: Northgate Technologies, Inc., Elgin, IL (US)

( * ) Notice: Subject to any disclaimer, the term of this patent is extended or adjusted under 35 U.S.C. 154(b) by 256 days.

(21) Appl. No.: 11/833,399

(22) Filed: Aug. 3, 2007

(65) Prior Publication Data
US 2008/0033344 A1 Feb. 7, 2008

Related U.S. Application Data (60) Provisional application No. 60/835,566, filed on Aug. 4, 2006.

(51) Int. Cl.
A61B 17/06 (2006.01)
A61M 39/04 (2006.01)
A61M 39/20 (2006.01)

(52) U.S. Cl.
USPC .............................. 606/213; 604/27

(58) Field of Classification Search
USPC ............ 600/208, 201, 114; 604/204, 27, 174, 604/891.1, 513, 539, 206, 201, 114, 604/164.01–164.06, 164.08; 607/40, 4; 606/213–216
See application file for complete search history.

(56) References Cited

U.S. PATENT DOCUMENTS

| | | |
|---|---|---|
| 2,722,935 A | 11/1955 | Thompson et al. |
| 3,464,434 A | 9/1969 | Nielsen |
| 3,853,105 A | 12/1974 | Kenagy |
| 3,862,907 A | 1/1975 | Shimotsuma et al. |
| 3,982,533 A | 9/1976 | Wiest |
| 4,048,992 A | 9/1977 | Lindemann et al. |
| 4,109,656 A | 8/1978 | Goethel et al. |
| 4,207,887 A | 6/1980 | Hiltebrandt et al. |
| 4,245,979 A | 1/1981 | Ito |
| 4,464,169 A | 8/1984 | Semm |
| 4,640,260 A | 2/1987 | Perez |
| 4,676,774 A | 6/1987 | Semm et al. |
| 4,691,900 A | 9/1987 | Maeda |
| 4,699,173 A | 10/1987 | Röhling |

(Continued)

FOREIGN PATENT DOCUMENTS

| | | |
|---|---|---|
| EP | 0 369 764 B1 | 6/1994 |
| EP | 0 692 273 B1 | 1/1996 |
| EP | 0 937 478 A1 | 8/1999 |
| EP | 0 712 635 B1 | 5/2003 |
| EP | 1 477 119 A1 | 11/2004 |
| FR | 2 840 222 | 12/2003 |
| JP | 5-168714 | 2/1993 |
| JP | 63-84243 | 6/1998 |

(Continued)

OTHER PUBLICATIONS

International Search Report and Written Opinion of the International Searching Authority issued in international application No. PCT/IB2007/002249 on Sep. 10, 2008 (7 pages).

(Continued)

Primary Examiner — Bhisma Mehta
Assistant Examiner — Bradley Osinski
(74) Attorney, Agent, or Firm — Brinks Gilson & Lione (57) ABSTRACT An in-dwelling port for providing repeated entry to a body during and/or after an operation is described. The port may include an external portion secured to a body outside an incision and a collapsible insertion portion that is inserted through the incision. The collapsible portion collapses when no instrument or lumen is present to permits the body to return to substantially a normal profile around the incision.

28 Claims, 8 Drawing Sheets

(56) References Cited

U.S. PATENT DOCUMENTS

| | | | |
|---|---|---|---|
| 4,878,894 A | 11/1989 | Sutter, Jr. et al. | |
| 4,884,565 A | 12/1989 | Cocozza | |
| 4,905,497 A | 3/1990 | Shindo et al. | |
| 4,960,134 A | 10/1990 | Webster, Jr. | |
| 4,977,776 A | 12/1990 | Shindo et al. | |
| 4,984,564 A * | 1/1991 | Yuen | 600/207 |
| 5,006,109 A | 4/1991 | Douglas et al. | |
| 5,031,613 A | 7/1991 | Smith et al. | |
| 5,061,239 A | 10/1991 | Shiels | |
| 5,098,393 A * | 3/1992 | Amplatz et al. | 604/167.03 |
| 5,121,700 A | 6/1992 | Blackwell et al. | |
| 5,152,745 A | 10/1992 | Steiner et al. | |
| 5,246,419 A | 9/1993 | Absten | |
| 5,250,287 A | 10/1993 | Cocozza | |
| 5,273,531 A | 12/1993 | Knoepfler | |
| 5,292,304 A | 3/1994 | Mantell et al. | |
| 5,305,698 A | 4/1994 | Blackwell et al. | |
| 5,328,458 A | 7/1994 | Sekino et al. | |
| 5,342,299 A | 8/1994 | Snoke et al. | |
| 5,360,396 A | 11/1994 | Chan | |
| 5,362,310 A | 11/1994 | Semm | |
| 5,363,839 A | 11/1994 | Lankford | |
| 5,383,923 A | 1/1995 | Webster, Jr. | |
| 5,407,427 A * | 4/1995 | Zhu et al. | 604/26 |
| 5,411,474 A | 5/1995 | Ott et al. | |
| 5,411,988 A | 5/1995 | Bockow et al. | |
| 5,439,441 A | 8/1995 | Grirnsley et al. | |
| 5,464,008 A | 11/1995 | Kim | |
| 5,478,837 A | 12/1995 | Rodgers et al. | |
| 5,496,408 A | 3/1996 | Motoda et al. | |
| 5,514,087 A | 5/1996 | Jones | |
| 5,514,133 A * | 5/1996 | Golub et al. | 606/1 |
| 5,534,261 A | 7/1996 | Rodgers et al. | |
| 5,537,993 A | 7/1996 | Reichert et al. | |
| 5,542,412 A | 8/1996 | Century | |
| 5,554,112 A | 9/1996 | Walbrink et al. | |
| 5,558,668 A | 9/1996 | Lankford et al. | |
| 5,578,305 A | 11/1996 | Franz et al. | |
| 5,586,974 A | 12/1996 | Martinez et al. | |
| 5,599,297 A | 2/1997 | Chin et al. | |
| 5,634,911 A * | 6/1997 | Hermann et al. | 604/256 |
| 5,642,730 A | 7/1997 | Baran | |
| 5,657,963 A * | 8/1997 | Hinchliffe et al. | 251/149.1 |
| 5,664,560 A | 9/1997 | Merrick et al. | |
| 5,728,223 A | 3/1998 | Murakami et al. | |
| 5,800,381 A | 9/1998 | Ognier | |
| 5,873,819 A | 2/1999 | Koch | |
| 5,899,208 A * | 5/1999 | Bonadio | 128/897 |
| 5,911,757 A * | 6/1999 | Seare, Jr. | 604/174 |
| 5,934,274 A | 8/1999 | Merrick et al. | |
| 5,964,223 A | 10/1999 | Baran | |
| 5,979,474 A | 11/1999 | Manako | |
| 5,980,835 A | 11/1999 | Porozni | |
| 6,024,736 A * | 2/2000 | de la Torre et al. | 606/1 |
| 6,033,390 A | 3/2000 | Von Dyck | |
| 6,033,426 A * | 3/2000 | Kaji | 606/213 |
| 6,051,241 A | 4/2000 | Briend et al. | |
| 6,068,703 A | 5/2000 | Chen et al. | |
| 6,076,745 A | 6/2000 | Primdahl | |
| 6,079,413 A | 6/2000 | Baran | |
| 6,085,556 A | 7/2000 | Moon | |
| 6,092,364 A | 7/2000 | Stellwagen | |
| 6,116,240 A | 9/2000 | Merrick et al. | |
| 6,165,201 A | 12/2000 | Sawhney et al. | |
| 6,203,519 B1 | 3/2001 | Fagerstrom et al. | |
| 6,240,943 B1 | 6/2001 | Smith | |
| 6,267,746 B1 | 7/2001 | Bumbalough | |
| 6,299,592 B1 | 10/2001 | Zander | |
| 6,379,373 B1 | 4/2002 | Sawhney et al. | |
| 6,428,500 B1 | 8/2002 | Koninckx | |
| 6,526,976 B1 | 3/2003 | Baran | |
| 6,537,246 B1 | 3/2003 | Unger et al. | |
| 6,551,270 B1 * | 4/2003 | Bimbo et al. | 604/93.01 |
| 6,579,279 B1 | 6/2003 | Rabiner et al. | |
| 6,679,873 B2 | 1/2004 | Rabiner et al. | |
| 6,719,960 B1 | 4/2004 | Hills et al. | |
| 6,729,334 B1 | 5/2004 | Baran | |
| 6,764,461 B2 * | 7/2004 | Mickley et al. | 604/15 |
| 6,802,832 B2 | 10/2004 | Rabiner et al. | |
| 6,821,287 B1 * | 11/2004 | Jang | 606/194 |
| 6,872,189 B2 | 3/2005 | DeLegge | |
| 6,896,665 B2 | 5/2005 | Picha et al. | |
| 6,949,092 B1 | 9/2005 | Moss | |
| 7,027,851 B2 | 4/2006 | Mejia | |
| 7,052,454 B2 * | 5/2006 | Taylor | 600/114 |
| 7,097,632 B2 * | 8/2006 | Shia et al. | 604/77 |
| 7,163,510 B2 * | 1/2007 | Kahle et al. | 600/208 |
| 7,172,085 B2 | 2/2007 | Beaudette | |
| 7,195,590 B2 * | 3/2007 | Butler et al. | 600/207 |
| 7,220,253 B2 | 5/2007 | Kantsevoy et al. | |
| 7,255,675 B2 | 8/2007 | Gertner et al. | |
| 7,300,399 B2 * | 11/2007 | Bonadio et al. | 600/208 |
| 7,344,547 B2 * | 3/2008 | Piskun | 606/185 |
| 7,367,963 B2 | 5/2008 | Cise et al. | |
| 7,377,898 B2 * | 5/2008 | Ewers et al. | 600/208 |
| 7,393,322 B2 * | 7/2008 | Wenchell | 600/208 |
| 7,404,807 B2 | 7/2008 | Callaway | |
| 7,452,347 B2 | 11/2008 | DeLegge | |
| 7,470,251 B2 | 12/2008 | Shah | |
| RE41,159 E | 3/2010 | Bourguignon | |
| 7,670,279 B2 | 3/2010 | Gertner | |
| 7,699,817 B2 | 4/2010 | Adams | |
| 7,699,818 B2 | 4/2010 | Gilbert | |
| 7,740,620 B2 | 6/2010 | Gilbert et al. | |
| 7,744,308 B2 | 6/2010 | Bussey, Jr. et al. | |
| 7,751,868 B2 | 7/2010 | Glossop | |
| 7,771,396 B2 | 8/2010 | Stefanchik et al. | |
| 7,794,436 B2 | 9/2010 | Pinel | |
| 2002/0068923 A1 * | 6/2002 | Caldwell et al. | 606/1 |
| 2002/0082584 A1 | 6/2002 | Rosenman et al. | |
| 2002/0183715 A1 | 12/2002 | Mantell et al. | |
| 2004/0153027 A1 | 8/2004 | Mantell | |
| 2005/0010164 A1 | 1/2005 | Mantell | |
| 2005/0113858 A1 * | 5/2005 | Deutsch | 606/195 |
| 2005/0125002 A1 | 6/2005 | Baran | |
| 2005/0137529 A1 | 6/2005 | Mantell | |
| 2005/0137592 A1 | 6/2005 | Nguyen et al. | |
| 2007/0270654 A1 * | 11/2007 | Pignato et al. | 600/208 |
| 2008/0103366 A1 * | 5/2008 | Banchieri et al. | 600/208 |
| 2008/0147114 A1 * | 6/2008 | Derowe et al. | 606/213 |

FOREIGN PATENT DOCUMENTS

| | | |
|---|---|---|
| WO | 93/17744 | 9/1993 |
| WO | 94/00484 | 1/1994 |
| WO | 96/29987 | 10/1996 |
| WO | 96/40090 | 12/1996 |
| WO | 00/69511 | 11/2000 |

OTHER PUBLICATIONS

International Preliminary Report on Patentability issued in international application No. PCT/IB2007/002249 on Apr. 2, 2009 (5 pages).

Office Action issued in Canadian application No. 2,660,050, dated Apr. 15, 2013 (3 pages).

* cited by examiner

IN-DWELLING PORT FOR ACCESS INTO A BODY

CROSS-REFERENCE TO RELATED APPLICATION

This application claims the benefit of U.S. Application No. 60/835,566 filed Aug. 4, 2006 and the entirety of that application is incorporated herein by reference.

TECHNICAL FIELD

This application relates to medical devices for use in surgical applications. More specifically, this application relates to ports for use in accessing an area of a body during and/or after a surgical procedure.

BACKGROUND

In minimally invasive surgical procedures, such as laparoscopic procedures, one or more small incisions are made in a body to allow access for the necessary surgical tools. If there is a need to re-enter the body after a surgical procedure, a mechanism for doing so must be put in place. For targeted or prophylactic chemotherapy, post-operative applications of a substance can be made by re-instituting an environment in the patient in which subsequent applications of the substance may be made. This may be accomplished by leaving a port device in the patient after the surgical procedure, or by surgically placing a port in the patient in preparation of a non-surgical treatment regimen.

The port may be a device capable of providing a sanitary access point to a body, where the device is a resealable mechanism that attaches to the exterior of the skin and the interior wall of the skin. The port permits a device for applying a substance to the body to be reconnected to the patient at a later time to apply the substance or other treatment. One example of this type of port is an enteral feeding tube port.

The design of re-entry ports typically focuses on semi-rigid tubes, such as feeding ports which are meant to transverse from out side the body into an organ such as the stomach. These devices often have a bulb or protrusion at the insertion end to maintain the location of the tube in the organ being accessed, and consist of a rigid or semi-rigid tube or lumen. Catheters, such as urethral catheters for access into the bladder tend to be flexible catheters, usually with a balloon or some type of protrusion that is used to anchor the catheter into the organ to prevent its movement back through the body channel. Intravenous ports, ports or needles that are inserted into a vein, are generally taped or perhaps sutured in place to prevent the accidental removal of the device. Other devices such as flat tubes with holes, sometimes under suction have been used as drains for wounds or to prevent fluid build up in the chest cavity.

SUMMARY

An improved port is described below that can remain in place, for example between physical structures such as the abdominal wall and the organs below, or in the plural cavity between the ribs and the lungs, or in any other physical location where the separation of bodily spaces may be required on a recurring basis.

According to a one aspect, an in-dwelling port is described having an external portion or flange configured for placement outside of an incision and defining a proximal port opening. A collapsible insertion portion having a distal port opening is attached to the external portion and positioned in a substantially coaxial relationship to the proximal port opening. The collapsible insertion portion is repeatably adjustable between an elongated position, where the collapsible insertion portion defines an elongated length and an elongated width, and a collapsed position, where the collapsible portion defines a collapsed length and a collapsed width. The elongated length is greater than the collapsed length and the elongated width is less than the collapsed width to allow for easy insertion, firmer placement in a collapsed position, and a less intrusive and disruptive way of leaving a port in a body when the port is not in use.

Other features and advantages of the invention will become apparent upon review of the following drawings, detailed description and claims.

DETAILED DESCRIPTION

FIGS. 1-4 illustrate one version of an in-dwelling port 10 where separation of body spaces may be required on a recurring basis. This in-dwelling port 10 may be used to reinflate the space between the abdominal wall and the organs below (peritoneal cavity). The port 10 includes an outer flange 12 and a collapsible insertion portion 14. The outer flange 12 may have a greater diameter than that of the collapsible insertion portion 14 to stabilize the port in the patient and prevent over-insertion into an incision. A proximal port opening 16 is defined by the flange 12 to allow one or more lumens or medical devices access into the collapsible insertion portion 14. A distal port opening 18 is positioned at the end of the collapsible insertion portion 14 and permits access to the body cavity.

A replaceable plug 20 is removably insertable into the proximal port opening to prevent an infection or other foreign substances to enter the body when the in-dwelling port 10 is not in use. The plug 20 may be attached to the outer flange 12 by a tether 22. The tether may be formed from the same piece of material as the outer flange, or it may be a separate material attached to the outer flange 14. The plug may be a compression-style plug that is elastic enough to fill the proximal port opening 16 when pressed in place. Alternatively, the plug 20 may be a discrete component unattached by a tether. Any of a number of other fastening means, such as threaded ends, collapsible detents or other mechanisms may also be used to connect the plug and the proximal port opening.

The outer flange may include recessed regions 24 on one or more sides. The recessed regions may be sized to provide an anchor for sutures, adhesives or other devices for holding the in-dwelling port in place on the body. The outer flange may also be held in place by having an optional adhesive surface to keep it against the skin. The adhesive surface may be islands of adhesive positioned about the underside of the flange. Alternatively, to provide a more complete seal and to help prevent deterioration of the tissue through which the in-dwelling port is inserted, a continuous ring of adhesive or adhesive material may be positioned on the underside of the flange to prevent tearing and strengthen the integrity of the tissue surface. Thus, the in-dwelling port 10 may be affixed in a number of ways, individually or collectively, by suturing the recessed regions of the flange, adhering the underside of the flange to the outer tissue surface, and even covering the flange with an adhesive bandage (regular and medicated) to help keep it in place and to further help resist infection.

Figure 1:
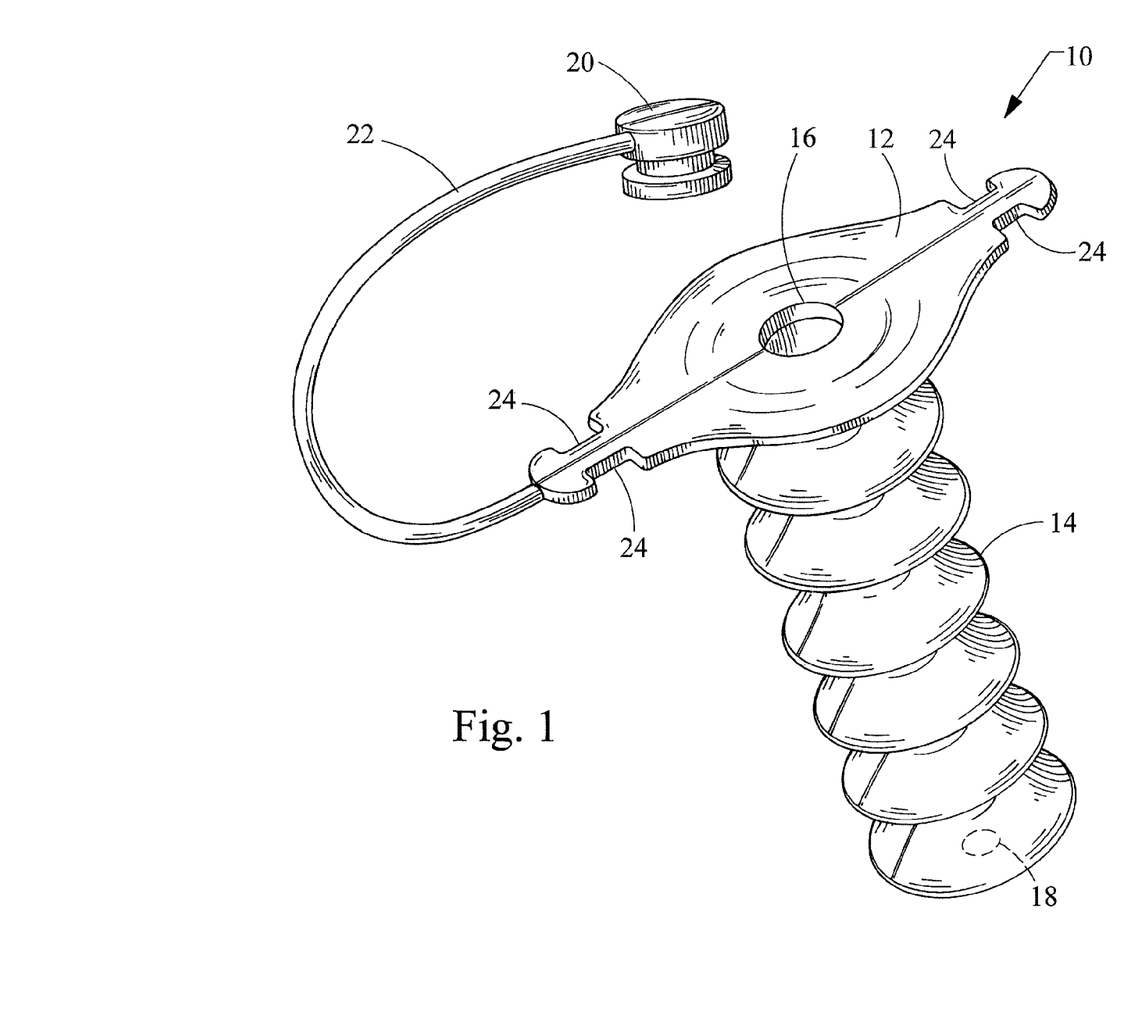
FIG. 1 is a perspective view of an in-dwelling port in an elongated position.
Figure 2:
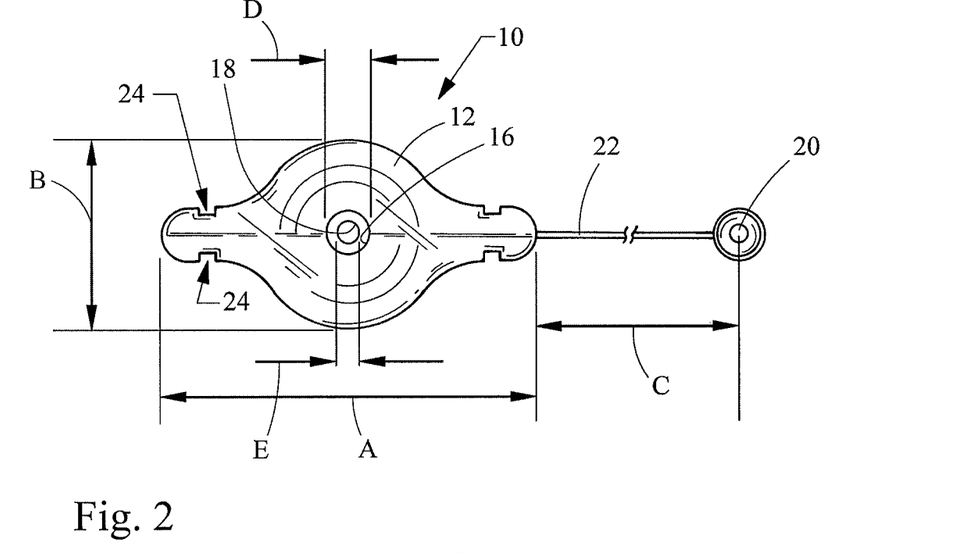
FIG. 2 is a top plan view of the in-dwelling port of FIG. 1.
Figure 3:
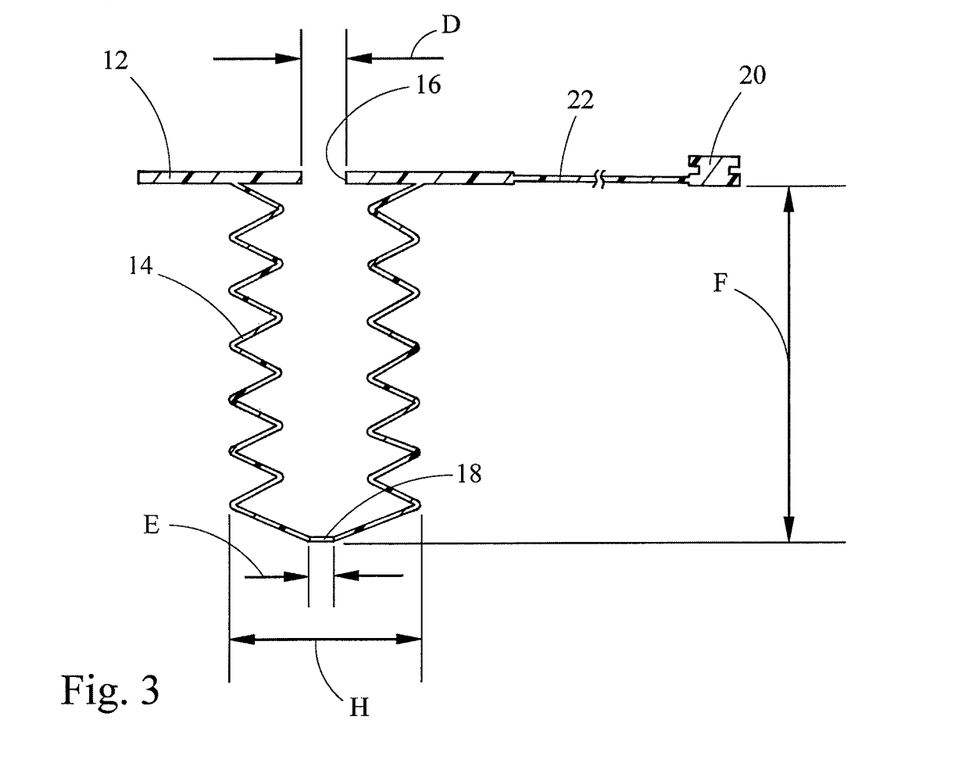
FIG. 3 is a cross-sectional side view of the port of FIG. 1.
Figure 4:
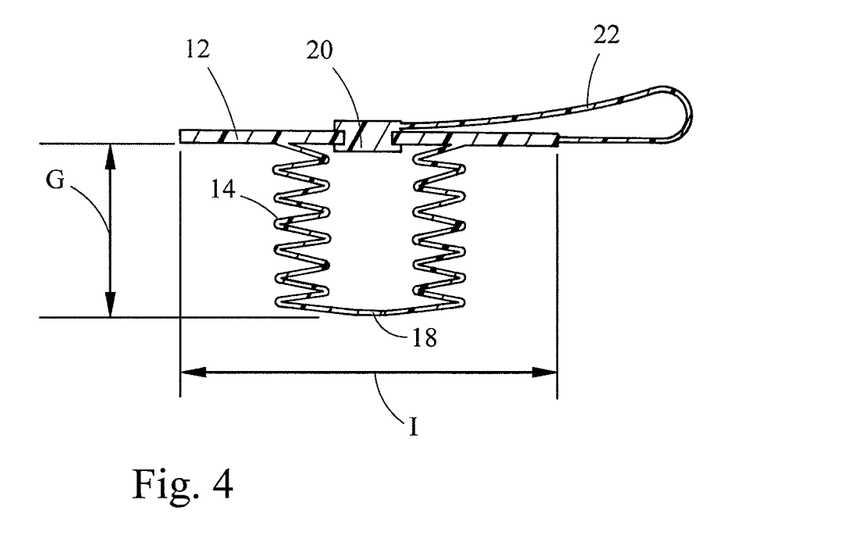
FIG. 4 is a cross-sectional side view of the port of FIG. 1 in a collapsed position.

The collapsible insertion portion 14 of the in-dwelling port 10 may be fabricated in any manner that permits it to collapse when not in use, for example in the form of a bellows or accordion-like structure. Once past the abdominal wall or other body structure, it can gently collapse back to an almost flat shape. The flat shape may assist in reducing irritation and trauma, as well as provide very little restriction to normal body motion and limited visibility of its presence. A feature of the bellows structure of the collapsible insertion portion is that it will present a reduced diameter when elongated and may more easily go through a relatively small incision or wound site, or even a natural body passage way. Once in place, the structure will allow the collapsible insertion portion to collapse into a larger diameter so as not to work itself out of the incision, wound, or body passage. Referring to FIG. 4, the collapsed state of the in-dwelling port expands the bellows portion to hold, for example, the abdomen wall between the flange 12 and the collapsible insertion portion 14 for a secure and low-profile point of re-entry.

Figure 5:
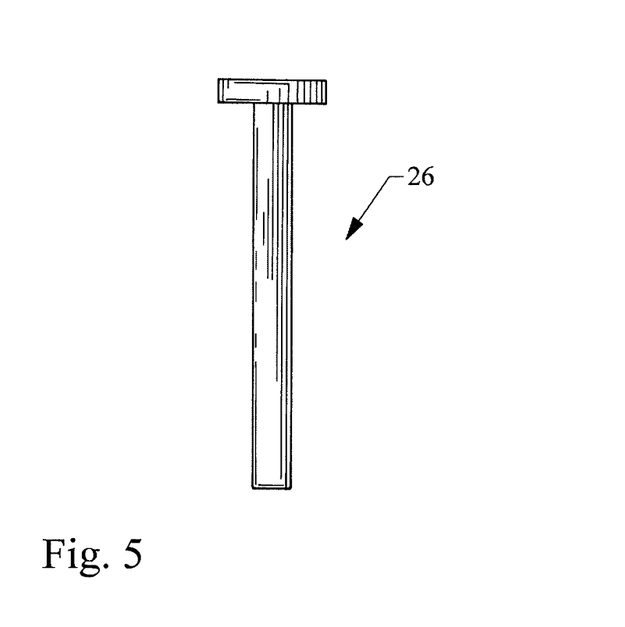
FIG. 5. is a side view of a stylus suitable for use in inserting the port of FIG. 1 into an incision.

Referring to FIG. 5, a stylus 26 is designed to fit in the collapsible insertion portion 14 via the proximal port opening 16 and extend the in-dwelling port 10 to its smallest diameter for insertion into an incision. If, for example, the in-dwelling port was intended for insertion into an abdomen wall, the stylus would first be inserted into the proximal port, extending the collapsible insertion portion and thus reducing its diameter. The distal port opening 18 may be provided with a smaller diameter than the proximal port opening 16 so that the stylus 26 remains in the collapsible insertion portion during insertion. A physician may then push the in-dwelling port into position from outside the abdomen wall and into the peritoneum, for example via a trocar wound (not shown).

Once inserted, and optionally secured at the flange to the abdomen, the stylus 26 would typically be removed and one or more lumens may be introduced and later reintroduced, through the in-dwelling port. The in-dwelling port 10 may allow for the insertion of medical devices after placement by maintaining one or more access lumens to pass a medical device through it such as a catheter, or a small needle or trocar, an optical endoscope, an operative instrument or any number of surgical, diagnostic, or palliative devices.

When all lumens in the port 10 are removed and the port is not in use, the collapsible insertion portion will collapse down and allow the abdomen wall to collapse to a more relaxed position that may be substantially close to its pre-insertion shape. The plug 20 may then be inserted to provide a barrier to contaminants. Having a way to allow the separation (or re-separation) of the abdominal wall or cavity from the organs below for purposes of examination, application of medicines, or even operative tasks is desirable and is usually accomplished by insufflation of the peritoneal space. Because the port is intended for access to the bodily space for the purpose of re-expanding the separation of one layer or body structure from another the port also permits the body structure to return to its substantially normal (collapsed) position.

Figure 6:
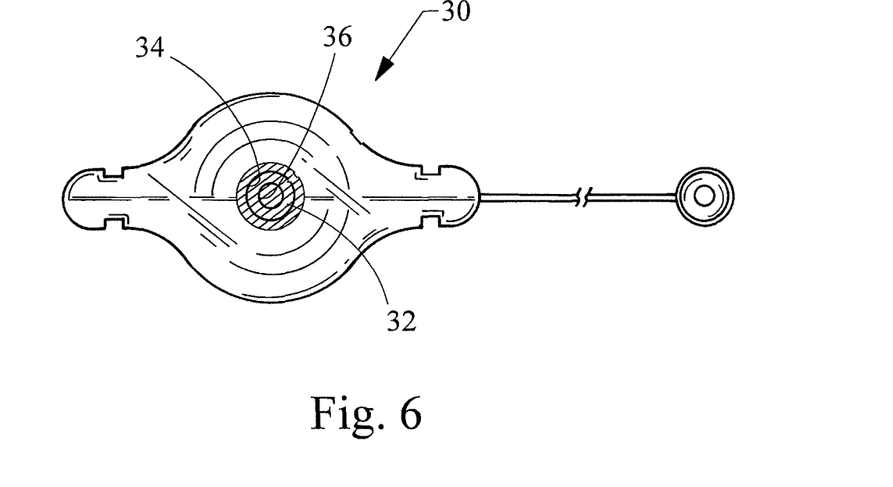
FIG. 6 is a top plan view of an alternative embodiment of the in-dwelling port of FIG. 1.
Figure 7:
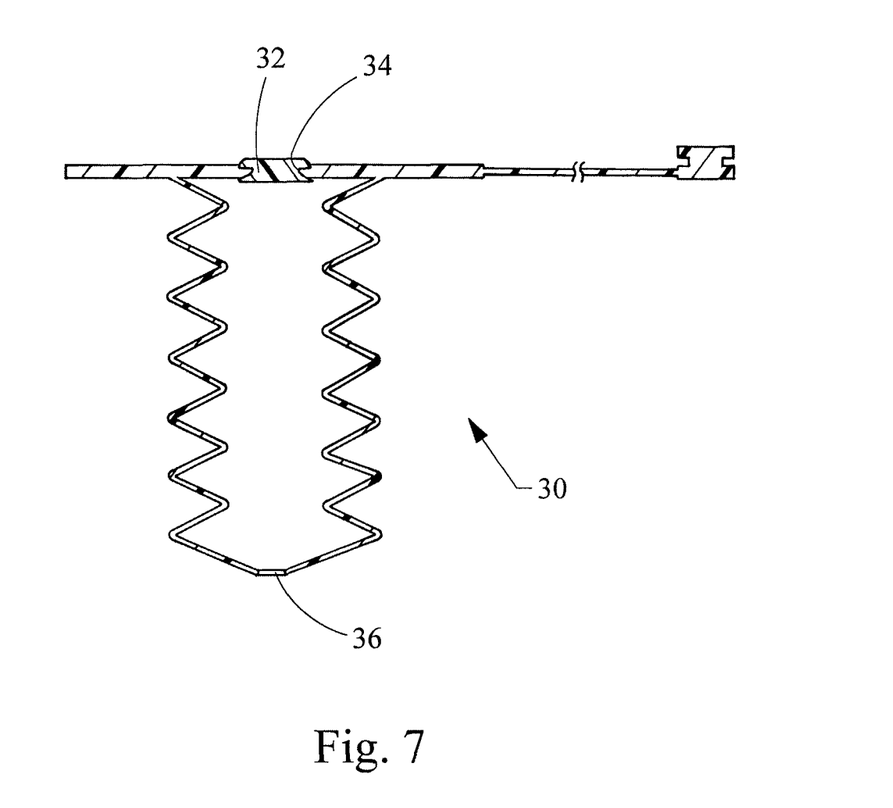
FIG. 7 is a cross-sectional side view of the port of FIG. 6 in an elongated position.

An alternative embodiment of the in-dwelling port 30 is shown in FIGS. 6-7. In this arrangement, a re-sealable membrane 32 is positioned across the proximal port opening 34. A needle or other sharp-ended introducing device may be used to pierce the membrane 32 or surface and introduce a lumen or instrument through the membrane and subsequently into the body via the distal port opening 36. The membrane would reseal itself after removal. This pierceable membrane or cover may be manufactured from any of a number of materials, for example polysoprene, isoprene or silicone. In an alternative embodiment, the in-dwelling port may have a second proximal port opening that could be connected to a filter in order to release pressure from an expanded space, for example the peritoneum during a laparoscopic procedure, without permitting organisms to be released into the air.

Figure 8:
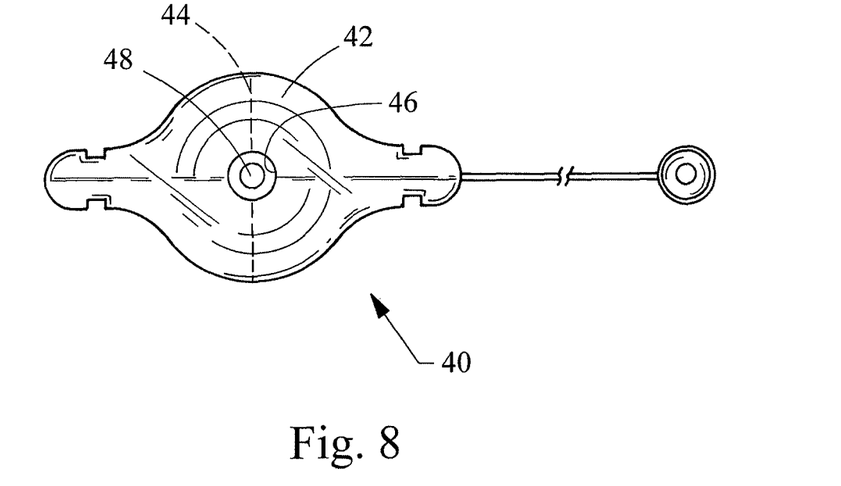
FIG. 8 is a top plan view of a second alternative embodiment of the in-dwelling port of FIG. 1.
Figure 9:
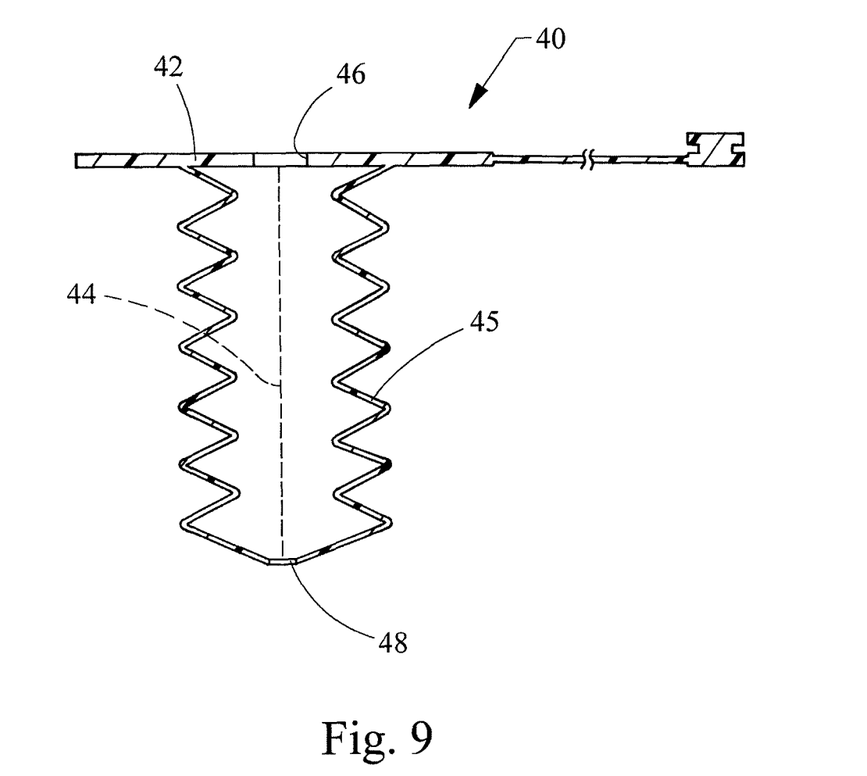
FIG. 9 is a cross-sectional side view of the port of FIG. 8 in an elongated position.

In an alternative embodiment shown in FIGS. 8-9, the in-dwelling port 40 may have a tear-away seam 44 disposed along the entire length of the port. The seam 44 may traverse the flange 42 and the collapsible insertion portion 45 to form a continuous line of perforations from the proximal port opening 46 to the distal port opening 48. In one embodiment, the seam 44 may be a line of perforations extending longitudinally down the device from proximal 46 to distal 28 port opening, multiple parallel lines of perforations to allow for tearing the indwelling port from one or more sides of the flange 42, or any desired pattern of perforations to allow segmented destruction and removal of the indwelling port. In alternative embodiments, the lines of perforations may be other types of weakened seams defining a continuous line of weakened or reduced thickness material that permit for a substantially clean tear when a user desires to remove the in-dwelling port.

One advantage of an in-dwelling port as shown in FIGS. 8-9 with a tear-away seam is that a new in-dwelling port may be inserted into an old indwelling port already positioned in a body and the old port could be removed by splitting and pulling out the old port. Alternatively, the old port could pulled into a sleeve device and removed, the sleeve serving to keep the space open to place a new port in place of the old port, or even a tool or a finger could be pushed along side the old port while a new port is positioned next to the tool or finger, and inserted.

The in-dwelling ports in FIGS. 1-9 are shown with one lumen through the center. In other implementations, two or more lumens may be fabricated so that more than instrument could be inserted into it, or one lumen could be attached to a pressure source such as an insufflator and the other to a suction source, or a commercially available pressure relief device (such as manufactured by Smart products), or a mini-endoscope may be inserted into one lumen an and instrument or catheter or some other operative device may be inserted into another. The device is not limited to a single useful lumen, and multiple lumens could be utilized with many other medical devices seeking entry into the body space. Other uses for the lumen(s) may include applications requiring the insertion of a fluid catheter, the use of an aerosolization or nebulizing device for the purpose of coating or treating organ cavity.

Figure 10:
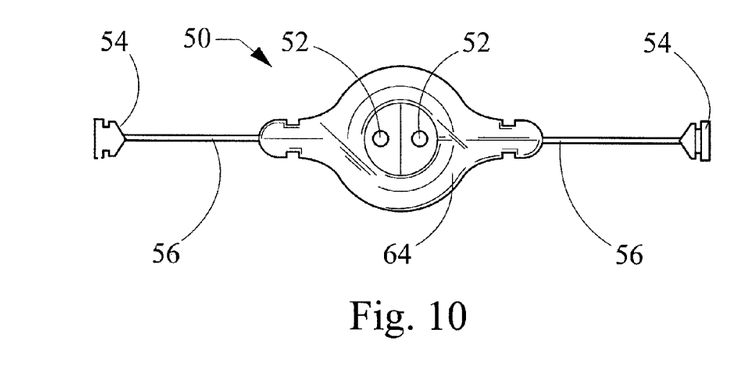
FIG. 10 is a top plan view of a third alternative embodiment of the in-dwelling port of FIG. 1.
Figure 11:
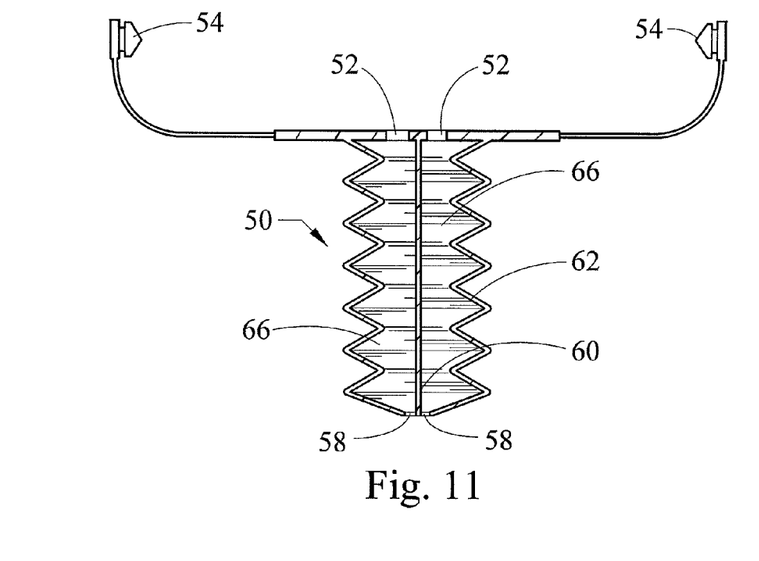
FIG. 11 is a cross-sectional side view of the port of FIG. 10 in an elongated position.
Figure 12:
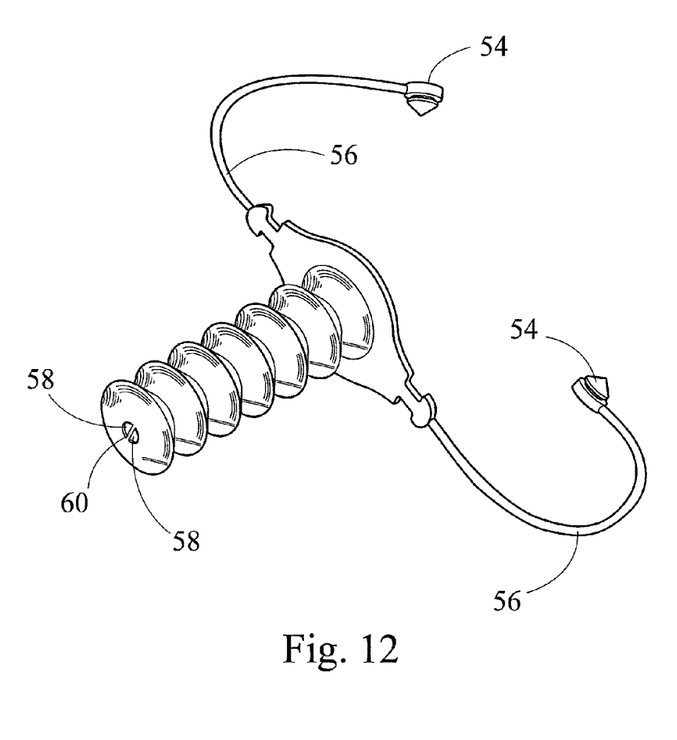
FIG. 12 is a perspective view of the port of FIG. 11.

As shown in FIGS. 10-12, an in-dwelling port 50 may be constructed with two proximal openings 52 that each lead to a respective half of the interior of a single collapsible insertion portion 62. Each proximal opening 52 may have its own removable plug 54 attached to the flange 64 by respective tethers 56. A collapsible partition 60 extending through the interior of the area enclosed by the collapsible insertion portion 62 defines two separate access paths 66 terminating at respective distal openings 58. Although the access paths 66 are shown as equal in size in FIGS. 10-12, access paths of unequal size or more than two paths in the single collapsible portion 62 are contemplated as well.

Figure 13:
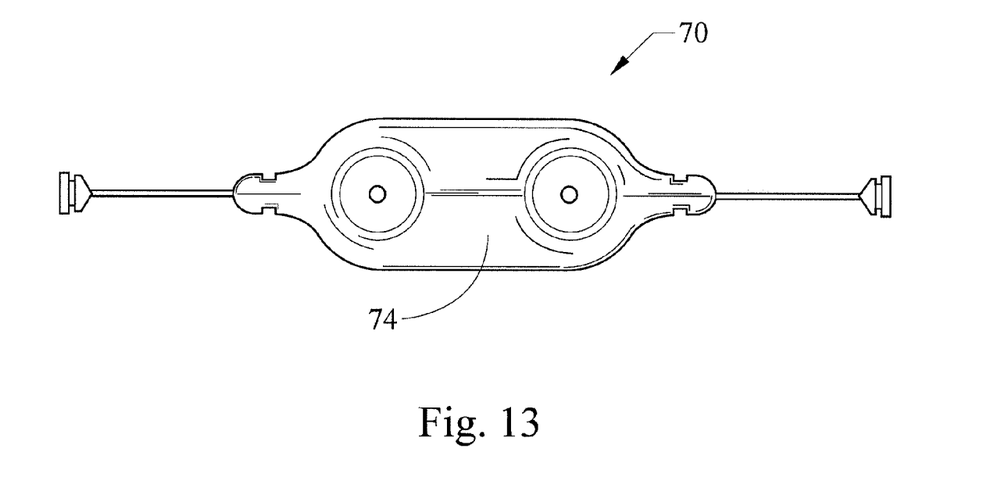
FIG. 13 is a top plan view of a fourth alternative embodiment of the in-dwelling port of FIG. 1.
Figure 14:
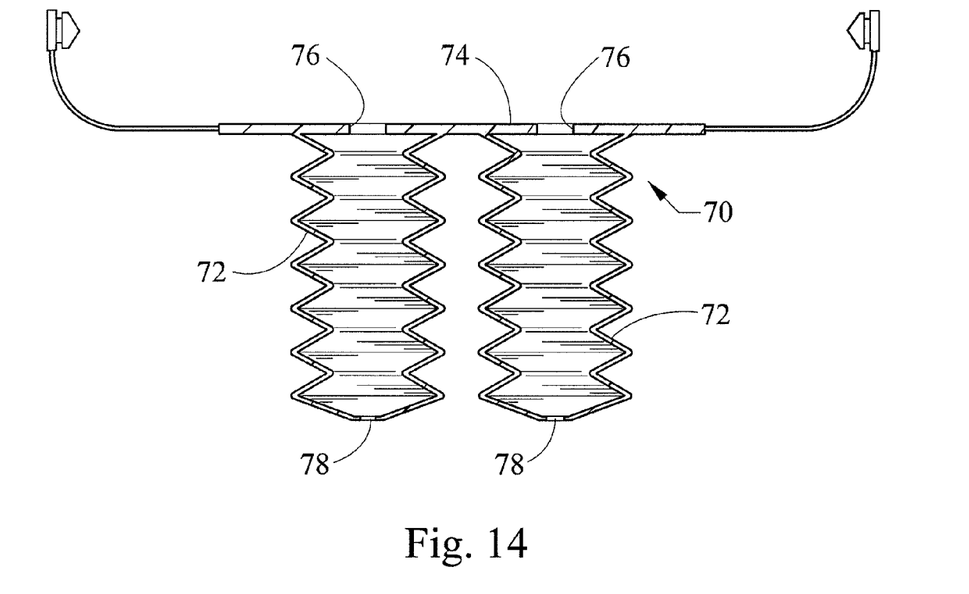
FIG. 14 is a cross-sectional side view of the port of FIG. 13 in an elongated position.

FIGS. 13 and 14 illustrate another version of an in-dwelling port 70 for allowing access for multiple devices such as noted above. In the version of FIGS. 13-14, two completely separate collapsible insertion portions 72 are formed in a single flange member 74. Each collapsible portion has its own proximal and distal opening 76, 78, where the proximal openings 76 may have a greater radius than the distal openings 78 or may be covered with a membrane suitable for piercing by a needle or other sharp instrument. Additionally, one or both collapsible portions may be partitioned internally as shown in FIGS. 10-12 to provide separate access for even more devices or instruments into a body cavity.

Figure 15:
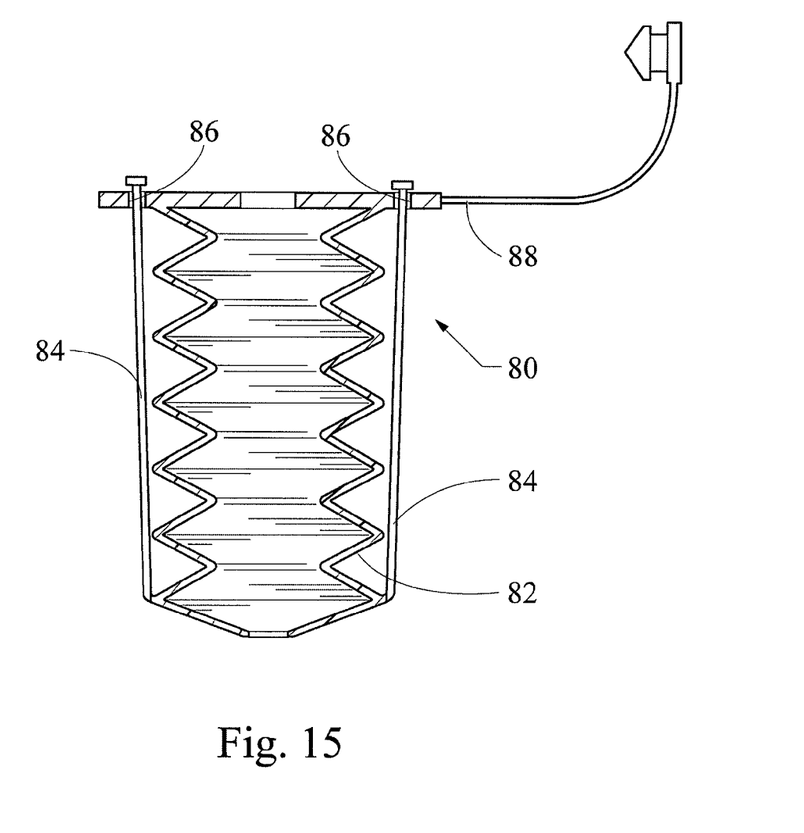
FIG. 15 is a cross-sectional side view of a fifth alternative embodiment of the port of FIG. 1 in an elongated position.
Figure 16:
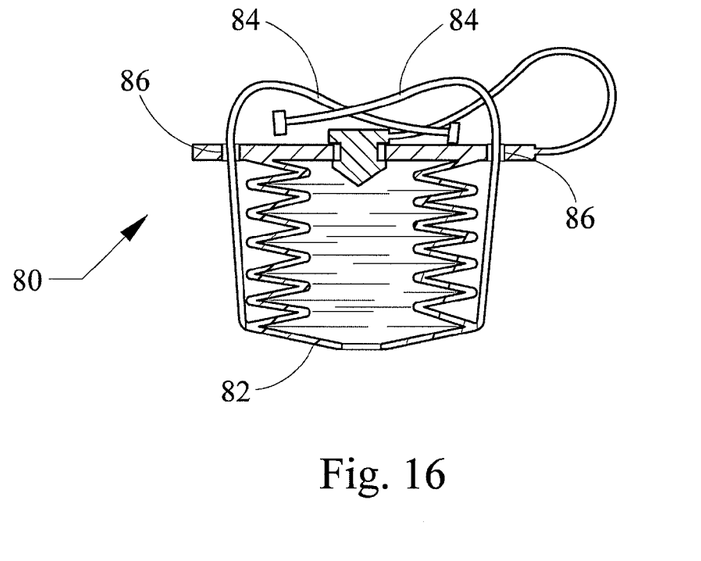
FIG. 16 is a cross-sectional side view of the port of FIG. 15 in a collapsed position.

Although the example of in-dwelling ports described above include collapsible insertion portions, shown as bellows, that are expandable into a body cavity, there may be a need to insure that the collapsible insertion portion or bellows of the device stays up to the distal surface (i.e. the interior surface) of the tissue or organ into which the device is inserted. FIGS. 15-16 illustrate an implementation of an in-dwelling port 80 that allows for the collapsible insertion portion 82 to remain secure, and prevent it from "relaxing" or loosening and becoming partially extended in the bodily cavity. This is accomplished by having one or more threads or tethers 84 attached to the distal portion of the insertion portion, which can be used to draw-up or retract the collapsible insertion portion 82, either through holes 86 in the top flange 88, or along the outside of the collapsible insertion portion 82 and the outside(s) of the top flange to be secured by some means such as tying, suturing, taping or any other method of securing the tether(s) 84 in such a way as to keep the collapsible insertion portion 82 collapsed, or loosening them to allow the collapsible insertion portion 82 to be expanded. The tethers 84 can be constructed of the same material as the in-dwelling port 80, from thread, or from any other flexible thin material. It could be accomplished with one or more such tethers 84. The tethers 84 can be attached to the collapsible insertion portion 82 in the molding process, by heat sealing (melting), tying, gluing, or any other method of attaching the tethers to the collapsible insertion portion of the device.

In yet additional alternative embodiments, where additional rigidity of the collapsible insertion portion may be desired, a stylus such as shown in FIG. 5 may include a central bore through which instruments or lumens may be inserted. Such a modified stylus may remain in the indwelling port during a procedure and removed to allow the in-dwelling port to collapse when not in use Any of the in-dwelling port versions described above may be coated or impregnated with antibacterial and or antimicrobial medications to prevent infection from occurring during its time in place. Such a coating for example could consist of, but is not limited to, Rifamacin, Rifampin, Minocycline, silver sulfadiazine, or Bardex R IC.

The in-dwelling port may be constructed of a resilient material that has the ability to reform its shape or accept a "retracted" shape after it is in place. Suitable materials include, but are not limited to, silicone, rubber, latex, nylon, and fabric like materials. Although any number of in-dwelling port sizes and dimensions are contemplated, and may vary depending on intended use, the example shown in FIG. 2 may have a flange major axis length A of 1.75 inches, a flange minor axis length B of 0.875 inches, and a tether length C of 0.875 inches. The proximal port opening diameter may be 0.196 inches and the distal port opening may be 0.112 inches. Accordingly, the stylus used to insert this specific version of the in-dwelling port would need to have a minimum diameter of greater than 0.112 inches and a maximum diameter of less than 0.196 inches. Referring again to FIGS. 3 and 4, the collapsible insertion portion in this example may have a collapsed depth G of 0.375 inches and a maximum extended depth F of 5.0 inches for a greater than 5 to 1 ratio. The extended diameter H of the collapsible insertion portion is preferably less than the collapsed diameter I, however the ratio may vary depending on, for example, the number and length of the folds that form the bellows or accordion-like structure of the collapsible insertion portion.

It is therefore intended that the foregoing detailed description be regarded as illustrative rather than limiting, and that it be understood that it is the following claims, including all equivalents, that are intended to define the spirit and scope of this invention.

I claim:

1. An in-dwelling port for permitting access into a body cavity, the port comprising:
    an external portion configured for placement outside of an incision and defining a proximal port opening, the proximal port opening having a proximal port opening diameter, and wherein the external portion has a first surface positioned to face away from a body and a second surface arranged to contact an external portion of a body surrounding the incision; and
    a flexible bellows portion configured to be movable inside the body cavity between an elongated position and a collapsed position, the flexible bellows portion having a first end attached to the second surface of the external portion and defining an unobstructed distal port opening opposite the first end, the unobstructed distal port opening having a distal port opening diameter, wherein the distal port opening diameter is less than the proximal port opening diameter; and
    wherein an internal passage of the flexible bellows portion is configured for continuous fluid communication with the body cavity via the unobstructed distal port opening.

2. The port of claim 1, further comprising a removable plug sized to seal the proximal port opening.

3. The port of claim 2, further comprising a tether connected with the plug at a first end and connected with the external portion at a second end.

4. The port of claim 1, wherein the external portion and the flexible bellows portion each comprise an antimicrobial material.

5. The port of claim 1, wherein the external portion and the flexible bellows portion each comprise a coating of antimicrobial material.

6. The port of claim 1, further comprising a tear-away seam extending at least a portion of a length of the flexible bellows portion and at least a portion of a width of the external portion.

7. The port of claim 6, wherein the tear-away seam comprises a line of perforations in the port.

8. The port of claim 6, wherein the tear-away seam comprises a region of weakened material.

9. The port of claim 1, further comprising an adhesive positioned along the second surface of the external portion and configured to adhere to tissue surrounding an incision through which the flexible bellows portion may be inserted.

10. The port of claim 9, wherein the adhesive comprises a continuous ring of adhesive.

11. The port of claim 1, wherein the external portion further comprises a pierceable surface resealably positioned over the proximal port opening.

12. An in-dwelling port for permitting access into a body, the port comprising:
  an external portion configured for placement outside of an incision and defining a proximal port opening, the proximal port opening having a proximal port opening diameter, wherein the external portion further comprises a pierceable membrane resealably positioned over the proximal port opening; and
  a collapsible insertion portion defining a distal port opening, the distal port opening having a distal port opening diameter, wherein the distal port opening diameter is less than the proximal port opening diameter;
  wherein the collapsible insertion portion is attached to the external portion and positioned in a substantially coaxial relationship to the proximal port opening, the collapsible insertion portion repeatably adjustable between an elongated position and a collapsed position within the body, while the external portion is affixed to an exterior of the body; and
  wherein the collapsible insertion portion is free of any portion that is configured to continuously anchor the in-dwelling port inside the body.

13. The port of claim 12, further comprising a removable plug sized to seal the proximal port opening.

14. The port of claim 13, further comprising a tether connected with the plug at a first end and connected with the external portion at a second end.

15. The port of claim 12, wherein the external portion and the collapsible insertion portion each comprise an antimicrobial material.

16. The port of claim 12, wherein the external portion and the collapsible insertion portion each comprise a coating of antimicrobial material.

17. An in-dwelling port for permitting access into a body, the port comprising:
  an external portion configured for placement outside of an incision and defining a proximal port opening, the proximal port opening having a proximal port opening diameter;
  a collapsible insertion portion defining a distal port opening, the distal port opening having a distal port opening diameter, wherein the collapsible insertion portion is configured for placement inside the body and comprises a plurality of folds positioned along a length of the collapsible insertion portion, the collapsible insertion portion attached to the external portion and adjustable between an elongated position and a collapsed position;
  wherein while the external portion is affixed to the body and the collapsible insertion portion is inside the body, the collapsible insertion portion is repeatedly collapsible or extendible within the body via unfolding of the plurality of folds or via folding of the plurality of folds; and
  wherein the proximal port opening diameter is greater than the distal port opening diameter.

18. The port of claim 17, wherein the proximal port opening diameter and the distal port opening diameter are less than 0.25 inches.

19. The port of claim 18, wherein the proximal port opening diameter is 0.196 inches and the distal port opening diameter is 0.112 inches.

20. The port of claim 1, wherein the flexible bellows portion is extendible in response to insertion through the proximal port opening of a device having a diameter less than the proximal port opening diameter and greater than the distal port opening diameter.

21. The port of claim 12, wherein the collapsible insertion portion is extendible in response to insertion through the proximal port opening of a device having a diameter less than the proximal port opening diameter and greater than the distal port opening diameter.

22. The port of claim 17, wherein the collapsible insertion portion is extendible in response to insertion through the proximal port opening of a device having a diameter less than the proximal port opening diameter and greater than the distal port opening diameter.

23. The port of claim 1, further comprising at least one retraction tether having a first end attached to a distal portion of the flexible bellows portion and a second end positioned on a side of the external portion opposite the flexible bellows portion, wherein the at least one retraction tether is movable relative to the external portion to retract the flexible bellows portion toward the external portion.

24. The port of claim 23, wherein the at least one retraction tether is positioned outside of the flexible bellows portion.

25. The port of claim 12, further comprising at least one retraction tether having a first end attached to a distal portion of the collapsible insertion portion and a second end positioned on a side of the external portion opposite the collapsible insertion portion, wherein the at least one retraction tether is movable relative to the external portion to retract the collapsible insertion portion toward the external portion.

26. The port of claim 25, wherein the at least one retraction tether is positioned outside of the collapsible insertion.

27. The port of claim 17, further comprising at least one retraction tether having a first end attached to a distal portion of the collapsible insertion portion and a second end positioned on a side of the external portion opposite the collapsible insertion portion, wherein the at least one retraction tether is movable relative to the external portion to retract the collapsible insertion portion toward the external portion.

28. The port of claim 27, wherein the at least one retraction tether is positioned outside of the collapsible insertion.

* * * * *

UNITED STATES PATENT AND TRADEMARK OFFICE
CERTIFICATE OF CORRECTION

| | | |
|---|---|---|
| PATENT NO. | : 8,663,271 B2 | Page 1 of 1 |
| APPLICATION NO. | : 11/833399 | |
| DATED | : March 4, 2014 | |
| INVENTOR(S) | : Robert R. Mantell | |

It is certified that error appears in the above-identified patent and that said Letters Patent is hereby corrected as shown below:

<u>In the Claims</u>

In column 6, claim 1, line 43, after "an external portion of" replace "a" with --the--.

Signed and Sealed this
Twenty-second Day of July, 2014

Michelle K. Lee
*Deputy Director of the United States Patent and Trademark Office*